(12) United States Patent
Duan et al.

US012257583B2

(10) Patent No.: US 12,257,583 B2
(45) Date of Patent: Mar. 25, 2025

(54) METHOD AND DEVICE FOR CONTROLLING MOVEMENT OF MICRO-PARTICLES IN SOLUTION USING ULTRA-HIGH FREQUENCY SOUND WAVE

(71) Applicant: Convergency (Tianjin) Biotech Ltd, Tianjin (CN)

(72) Inventors: Xuexin Duan, Tianjin (CN); Yang Yang, Tianjin (CN)

(73) Assignee: CONVERGENCY (TIANJIN) BIOTECH LTD., Tianjin (CN)

( * ) Notice: Subject to any disclaimer, the term of this patent is extended or adjusted under 35 U.S.C. 154(b) by 604 days.

(21) Appl. No.: 17/618,268

(22) PCT Filed: Jun. 15, 2020

(86) PCT No.: PCT/CN2020/096178
§ 371 (c)(1),
(2) Date: Dec. 10, 2021

(87) PCT Pub. No.: WO2020/249131
PCT Pub. Date: Dec. 17, 2020

(65) Prior Publication Data
US 2022/0333052 A1    Oct. 20, 2022

(30) Foreign Application Priority Data
Jun. 13, 2019 (CN) .......................... 201910512148.6

(51) Int. Cl.
| | |
|---|---|
| *B01L 3/00* | (2006.01) |
| *B01D 21/28* | (2006.01) |
| *B01J 19/10* | (2006.01) |
| *C12M 1/42* | (2006.01) |
| *C12M 3/06* | (2006.01) |
| *G01N 15/14* | (2024.01) |
| *G01N 15/1433* | (2024.01) |
| *G01N 15/10* | (2006.01) |

(52) U.S. Cl.
CPC ........ *B01L 3/502761* (2013.01); *B01D 21/28* (2013.01); *B01J 19/10* (2013.01); *B01L 3/502707* (2013.01); *B01L 3/502715* (2013.01); *C12M 1/42* (2013.01); *C12M 23/16* (2013.01); *C12M 35/04* (2013.01); *G01N 15/1433* (2024.01); *G01N 15/1459* (2013.01); *G01N 15/1484* (2013.01); *B01L 2200/0652* (2013.01); *B01L 2400/0439* (2013.01); *G01N 2015/1006* (2013.01); *G01N 2015/1027* (2024.01)

(58) Field of Classification Search
CPC ........ C12M 1/42; C12M 23/16; C12M 35/04; G01N 15/1433; G01N 15/1459; G01N 15/1484; G01N 2015/1006; G01N 2015/1027; B01L 3/502715; B01L 3/502761; B01L 3/502707; B01L 2200/0652; B01L 2400/0439; B01D 21/28; B01J 19/10
See application file for complete search history.

(56) References Cited

PUBLICATIONS

Cui et al., "Bulk Acoustic Wave Resonator Integrated Microfluidics for Rapid and High Efficiency Fluids Mixing and Bioparticle Trapping", IEEE International Ultrasonic Symposium, ISSN:1948-5727, pp. 1-3 (2016).*
Cui et al., Nanotechnology and Precision Engineering, vol. 2, pp. 15-22 (2019).*
Wu et al., PNAS, vol. 114, No. 40, pp. 10584-10589 (2017).*
Wu et al., Microsystems & Nanoengineering 5:32, pp. 1-18 (2019).*

* cited by examiner

*Primary Examiner* — John Kim
(74) *Attorney, Agent, or Firm* — John A. Miller; Shumaker, Loop & Kendrick, LLP (57) ABSTRACT

A microfluidic control system and method for controlling the movement of target particles in a fluid. The microfluidic system comprises a fluid channel which is provided with an inlet and a plurality of outlets, and one or more ultra-high frequency sound wave resonators which may generate a bulk acoustic wave having a frequency of about 0.5-50 GHz in the fluid channel; by means of adjusting the shape and orientation of a bulk acoustic wave generating region of the ultra-high frequency bulk acoustic wave resonator, the particles enter a vortex channel caused by the bulk acoustic wave in a solution and move according to the specified position and direction, and the particles in the solution may be controlled and separated to obtain specified particles, or obtain a purified solution after the particles are separated.

15 Claims, 5 Drawing Sheets

METHOD AND DEVICE FOR CONTROLLING MOVEMENT OF MICRO-PARTICLES IN SOLUTION USING ULTRA-HIGH FREQUENCY SOUND WAVE

This application claims priority to the following Chinese patent application: Application No. 201910512148.6, filed on Jun. 13, 2019 with a title of "Method and apparatus for controlling the movement of particles in a solution using ultra-high frequency acoustic waves", the entire contents of which are incorporated by reference in this application.

TECHNICAL FIELD

The present invention relates to the field of cell research methodology and medical devices. Specifically, the invention relates to a microfluidic system for the separation and analysis of cells or microvesicles and a method for using said system to separate and analyze cells or microvesicles.

BACKGROUND TECHNOLOGY

Cellular or subcellular particles present in human body fluids such as blood and tissue fluids, as well as biomolecular particles such as nucleic acids and proteins, are important for physiological health and research, and therefore a need exists to separate cellular or subcellular particles or biomolecular particles from body fluids. There are many methods in the prior art for separating particles such as cells by means of filters, but they all have disadvantages such as complicated operation, easy clogging, and low throughput.

The separation of particles in samples using microfluidic systems is an emerging technology. Most of the methods that have been reported are based on the physical properties of particles such as cells for separation, or based on biological specificity for differentiation and separation. These methods suffer from huge expense and low throughput.

Therefore, there is a great need for a system and method that enables the separation of cells or microvesicles or biomacromolecular particles in solution to obtain the desired cells or biomacromolecular particles, or the purified body fluid obtained after the removal of particles such as cells.

SUMMARY OF THE INVENTION

The present invention is the first to discover that the use of ultra-high frequency bulk acoustic waves can effectively manipulate the position and direction of movement of flexible particles such as cells or vesicles, or biomolecules such as nucleic acids or proteins or polysaccharides in solution in a microfluidic system, thereby providing methods and systems for separating and obtaining target cells or vesicles or biomolecule particles, or for obtaining a liquid after removal of particles such as cells or vesicles or biomolecules.

Specifically, the present invention provides a method for controlling the movement of flexible particles in a solution, comprising:

(1) causing a solution containing a target flexible particle to flow through a microfluidic device, said device comprising:
 a fluid channel having an inlet and an outlet channel;
 one or more UHF bulk acoustic wave resonators provided on a wall of said fluid channel, said UHF bulk acoustic wave resonators being capable of generating bulk acoustic waves at said fluid channel having a frequency of about 0.5-50 GHz transmitted to a wall on the opposite side of said fluid channel;

(2) said UHF resonator emitting a bulk acoustic wave transmitted to said wall on the opposite side of said fluid channel, generating a vortex channel in the solution defined (defined) by the boundary of the bulk acoustic wave producing region of the UHF resonator;

(3) causing the target flexible particles in the solution to enter and move along the vortex channel and leave the vortex channel at a set position.

Flexible particles are nano- or micron-sized particles with deformation properties. The flexible particles may be artificial or natural. Said particles may be micro-agglomerates with a membrane structure, in particular micro-agglomerates with a lipid bilayer or lipid-like bilayer, for example cells or vesicles, including exosomes, etc., or artificially prepared, for example liposomes or microcapsules in the form of water-in-oil formulations or water-in-oil-in-water (W/O/W) double emulsion formulations, etc. Said particles may also be of irregular shape, for example as biological macromolecules such as nucleic acids or proteins.

In one aspect, the present invention provides a method for controlling the movement of cells or vesicles in solution, comprising, (1) causing a solution containing a target cell or vesicle to flow through a microfluidic device, said device comprising:
 a fluidic channel having an inlet and an outlet channel;
 one or more ultra-high frequency bulk acoustic wave resonators provided on a wall of said fluid channel, said ultra-high frequency bulk acoustic wave resonators being capable of generating bulk acoustic waves at said fluid channel having a frequency of about 0.5-50 GHz transmitted to a wall on the opposite side of said fluid channel;

(2) said UHF resonator emitting a bulk acoustic wave transmitted to said wall on the opposite side of said fluid channel, generating a vortex channel in the solution defined by the boundary of the bulk acoustic wave generating region of the UHF resonator;

(3) causing a target cell or vesicle in the solution to enter and move along the vortex channel and to leave the vortex channel at a set position.

In the present invention, the cells or vesicles may be artificial or natural, and usually said particles are microclusters with a membrane structure, in particular microclusters with a lipid bilayer or a lipid-like bilayer. The flexible particles involved in the present invention typically have a diameter of about 0.01-30 um, preferably 0.2-25 um in diameter, more preferably 0.5-20 um. In one aspect of the present invention, said flexible particles are naturally occurring particles, such as cells or vesicles released by cells into the extracellular environment. Cells include cells of naturally occurring or cultured cells of plants or animals (e.g. mammals including humans), as well as unicellular organisms such as bacteria, fungi or simple multicellular organisms. Vesicles are microvesicles that are released into the extracellular environment by a variety of different animal cells. These cell-associated microvesicles are vesicle-like vesicles with a bilayer membrane structure that are shed from the cell membrane or secreted by the cell. They can have a diameter of about 30-1000 nm, about 30-800 nm, about 30-150 nm, or about 30-100 nm. Cell-released microvesicles include exosomes, microvesicles, vesicles, membrane vesicles, prostatic vesicles, microparticles, intratubular vesicles, intranuclear body-like vesicles, or cytosolic vesicles.

In one aspect, the present invention provides a method for controlling the movement of a target biological macromolecule such as a nucleic acid or protein or polysaccharide (particularly a nucleic acid) in a solution, comprising, (1) causing a solution containing a target biomolecule to flow through a microfluidic device, said device comprising:
   a fluid channel having an inlet and an outlet channel;
   one or more UHF bulk acoustic wave resonators which are provided on a wall of said fluid channel, said UHF bulk acoustic wave resonators being capable of generating bulk acoustic waves at said fluid channel at a frequency of about 0.5-50 GHz transmitted to a wall on the opposite side of said fluid channel;

(2) said UHF resonator emitting a bulk acoustic wave transmitted to said wall on the opposite side of said fluid channel, generating a vortex channel in the solution defined by the boundary of the bulk acoustic wave generating region of the UHF resonator;

(3) causing a target biomolecule in solution to enter and move along the vortex channel and to leave the vortex channel at a set position.

In one aspect of the present invention, the biological macromolecule in said method is a nucleic acid. As used herein, "nucleic acid" (and the equivalent term "polynucleotide") refers to a polymer of ribonucleosides or deoxyribonucleosides containing phosphodiester bonds between nucleotide subunits. Nucleic acids include, but are not limited to, genetic DNA, cDNA, hnRNA, mRNA, rRNA, tRNA, microRNA, fragmented nucleic acids, nucleic acids obtained from subcellular organelles such as mitochondria, and nucleic acids obtained from microorganisms or viruses that may be present on or in a sample. Nucleic acids include natural or synthetic, such as amplification reaction products using artificial or natural DNA or RNA as a template. Nucleic acids may be double-stranded or single-stranded, cyclic or linear. Samples that can be used to detect target nucleic acids include samples from cell cultures, eukaryotic microorganisms or diagnostic samples such as body fluids, body fluid sediments, gastric lavage samples, fine needle aspirates, biopsy samples, tissue samples, cancer cells, cells from patients, cells from tissues or cells cultured in vitro from individuals to be tested and/or treated for disease or infection, or forensic samples. Non-limiting examples of body fluid samples include whole blood, bone marrow, cerebrospinal fluid, peritoneal fluid, pleural fluid, lymphatic fluid, serum, plasma, urine, chyme, feces, ejaculate, sputum, nipple aspirate, saliva, swab samples, douche or lavage fluid, and/or wipe samples. The method of the present invention is particularly suitable for isolating nucleic acids (e.g., DNA and RNA in any form, including natural or synthetic nucleic acids, such as amplification reaction products using DNA or RNA as a template) of length ≥300 bp, preferably ≥1 kbp, more preferably ≥10 kbp, for example ≥50 kbp.

An ultra high frequency (UHF) bulk acoustic wave resonator in the present invention is a resonator capable of generating bulk acoustic waves with a frequency of higher than 0.5 GHz (preferably with a frequency of higher than 1 GHz), e.g., at frequencies of 0.5-50 GHz. Said UHF bulk acoustic wave resonator can be, for example, a thin-film bulk acoustic wave resonator or a solid-state assembly type resonator, etc.

In the method of the present invention, the UHF resonator emits UHF bulk acoustic waves transmitted to the opposite wall of said fluid channel (e.g., the top of the flow channel), and the attenuation of the bulk force generated by the acoustic wave in the fluid causes an acoustic jet in the flow-through solution, resulting in a localized three-dimensional vortex of the fluid in the microfluidic channel. Since the vortexes are generated by the volume force induced by the acoustic wave attenuation, the central axis of the vortex is above the boundary of the bulk acoustic wave generating region; the successive vortexes caused by the UHF bulk acoustic wave forms an acoustic fluid vortex channel, and the shape of the vortex channel is basically the same as the shape of the bulk acoustic wave action region, which is located above the boundary of the bulk acoustic wave generating region, i.e., the shape and location of the vortex channel are defined by the boundary of the bulk acoustic wave generation region of the UHF resonator.

In one aspect of the present invention, said fluid channel of the microfluidic device has an outflow channel for said flexible particles such as cells or vesicles, or biomolecules such as nucleic acids or proteins, etc. that are controlled to move, which may be referred to as a particle outflow channel. In another aspect of the present invention, said fluidic channel also has other outflow channels, such as an outflow channel for a solution that have removed or contains fewer of said cells or vesicles being controlled to move, which may be referred to as a solution outflow channel. The ratio of the width of the opening of said particle outflow channel and the solution outflow channel may be set to be about 1:1-1:20, preferably about 1:2-1:15, for example about 1:4-1:10. In one aspect of the present invention, the position at which said flexible particles leave the vortex channel is close to the opening of said particle outflow channel.

In step (3) of the above method, the shape and position of the bulk acoustic wave generating region of the UHF bulk acoustic wave resonator can be adjusted so that flexible particles (such as cells or vesicles), or biological macromolecules (such as nucleic acids or proteins) in solution enter the vortex channel and flow down along the channel and leave the vortex channel at a set position. Thereby said flexible particles leave the region of bulky acoustic effect in a specified position and follows a specified direction into a desired outflow channel, for example into said particle outflow channel. This specified position of leaving the vortex channel is named the release point, i.e. the position where said flexible particles leave the bulk acoustic wave effecting region. The solution excluding said controlled moving cells or vesicles then maintains the inflow direction and flow into the aforementioned solution outflow channel.

Since one of the important factors for the departure of flexible particles flexible particles (such as cells or vesicles), or biological macromolecules (such as nucleic acids or proteins) from the vortex channel is the effect of flow layer along the direction of the fluid channel, the release point is usually located in the downstream region of the vortex channel. In another aspect of the present invention, the release point is usually at the place where the vortex channel has a turn or change in curvature, i.e., above the position corresponding to a turn or a change in curvature of the boundary of the bulk acoustic wave effecting region, i.e., there is a turn or a change in curvature of the boundary of the bulk acoustic wave effecting region corresponding to said release point. Without being bound by the relevant theory, the applicant believes that the reason for this phenomenon lies in the fact that, at the turn or corner of the vortex channel, the direction of the vortex and the direction of the acoustic radiation force suddenly change; the flexible particles such as cells or vesicles, or biological macromolecules such as nucleic acids or proteins, are moving at the center of the vortex under the action of the acoustic radiation force; when these flexible particles arrive at the turn or corner of the vortex channel, in the case of biomolecules such as cells or vesicles or nucleic acids or proteins, particles that meet the right conditions (e.g., the right size and shape)

are able to change direction of motion with the vortex channel and quickly refocus to the center of the vortex channel after the turn, while particles that do not meet the conditions (e.g., have a smaller size) are more affected by the jump in layer drag direction and thus leave the vortex channel.

In one aspect of the present invention, the above method provided by the present invention is suitable for processing liquid samples containing a large number of flexible particles such as cells or vesicles, or nucleic acids or proteins, etc.; said large number of flexible particles can enter the vortex channel and move along it in a successive moving manner and leave the vortex channel at a set position, thus achieving fast and high throughput processing. In one aspect of the present invention, the above method provided by the present invention is suitable for processing samples containing a large number of cells or vesicles, such as whole blood or blood grades.

The above method provided by the present invention can be used to obtain or purify the desired flexible particles in a sample. In one aspect of the present invention, said method may be used to enrich the desired flexible particles.

The above method provided by the present invention can also be used to remove unwanted flexible particles from the sample and obtain a purified solution. In one of the aspects of the present invention, it is possible to remove certain cells or vesicles from a blood sample, for example to remove blood cells and obtain plasma.

In one aspect of the present invention, the method described above further comprises controlling the flexible particles entering the vortex channel and flowing along the vortex channel by adjusting the power of the bulk acoustic wave and/or by adjusting the velocity of flow of said solution through the bulk acoustic wave effecting region. The flexible particles that do not enter the vortex channel or that enter the vortex channel but leave the vortex channel before reaching the designated release point pass through the bulk acoustic wave region and flow out in the direction in which the sample entered the fluid channel.

In one aspect of the present invention, the boundary lines of the bulk acoustic wave generation region of the UHF resonator described above (i.e., the shape of the corresponding vortex channel) are set to accommodate the target flexible particles in the vortex channel and move along the vortex channel to the release point. This prevents the target flexible particles from leaving the vortex channel and not leaving the vortex channel from the release point asset.

In yet another aspect of the present invention, wherein the boundary shape of the bulk acoustic wave generation region of the UHF resonator is adjusted so that the target flexible particles remain in the vortex channel and move to the release point. The presence of turns or curvature variations in the boundary lines of the bulk acoustic wave generation region may increase the chance that the flexible particles break away from the vortex channel. Therefore, the efficiency of separation can be improved by reducing the presence of turns or curvature variations in the boundary lines of the bulk acoustic wave generation region to keep the flexible particles moving in the vortex channel, i.e., to reduce the number of flexible particles that break away from the vortex channel.

In yet another aspect of the present invention, the flexible particles are kept in the vortex channel while moving to the release point by adjusting the angle formed by the boundary line of the bulk acoustic wave generation region of said UHF resonator and the fluid channel. The inventor unexpectedly found that the smaller the angle between the boundary line of the bulk acoustic wave generating region and the fluid channel, the easier it is to keep the flexible particles moving in the vortex channel, i.e., fewer flexible particles leave the vortex channel, and thus improving the efficiency of separation.

In yet another aspect of the present invention, the bulk acoustic wave effecting region of the UHF bulk acoustic wave resonator in the microfluidic system has a focusing zone and a sieving zone. The focusing zone is located upstream of the bulk acoustic wave effecting region (i.e., near the direction of sample inflow and away from the release point), and the sieving zone is located downstream of the bulk acoustic wave action region (i.e., near the direction of sample outflow; nearer to or including the release point). The setup of the bulk acoustic wave effecting region in the focusing zone is more suitable to keep the flexible particles moving in the vortex channel compared to that of the sieving zone; cells or vesicles in the vortex channel in the focusing zone move along the same or similar direction as the flow direction and are subject to relatively less vortex dragging force, making it easier for the cells or vesicles to enter and remain in the vortex channel; in the downstream sieving zone, cells focused to the vortex center can move more stably along the vortex channel than unfocused cells. In yet another aspect of the present invention, the angle formed between the boundary line of the bulk acoustic wave effecting region and the fluid channel in the focusing zone is smaller than that in the sieving zone. For example, in the focus zone, the boundary of the bulk acoustic wave effecting region and the fluid channel direction is the same or basically the same (for example, the angle is less than 10°); the cells in this region of the vortex channel being effected by the vortex drag force which basically does not change the cell movement direction (i.e., the direction of the flow) but only let the cell move to the center of the vortex, thus achieve the focus of the cell; in sieve zone, angle between the boundary of the bulk acoustic wave effecting region and the fluid channel is bigger, the cells focused to the vortex center moves more stably in the vortex channel than the unfocused cells.

In the present invention, said microfluidic apparatus typically includes power adjusting device which adjusts the power of the bulk acoustic waves generated by said UHF resonator.

In the present invention, said microfluidic device typically includes a flow rate adjusting device which adjusts the rate of flow of said solution through the region affected by the bulk acoustic wave.

In one aspect of the present invention, wherein said cells comprise cell clusters. Said cell clusters typically comprise several, for example 2, 3, 4, 5, 6, 7, 8, 9 or 10, cells. In one aspect of the present invention, wherein said vesicles comprise a cluster of vesicles. Said cluster of vesicles typically comprises several, e.g. 2-50, vesicles.

In one aspect of the present invention, wherein said power adjusting device has an output power of about 20-5000 mW, preferably 50-2000 mW, more preferably 100-1500 mW.

In one aspect of the present invention, wherein said flow rate adjusting device adjusts the speed of said solution flow through the bulk acoustic region to be about 0.1-10 mm/s, preferably about 0.3-5 mm/s, more preferably about 0.5-3 mm/s.

In one aspect of the present invention, wherein said flow rate adjusting device regulates the speed of said solution flow through the bulk acoustic wave region to be about 0.01-100 μL/min, preferably about 0.1-50 μL/min, more preferably about 0.5-30 μL/min.

In one aspect of the present invention, wherein said fluid channel of the microfluidic device has a height of about 5-200 μm, preferably about 25-100 μm, more preferably about 30-80 μm, for example about 40-60 μm.

In one aspect of the present invention, wherein said UHF bulk acoustic wave resonator has a bulk acoustic wave generation area of about 500-200000 μm$^2$, preferably about 5000-50000 μm$^2$, most preferably about 10000-25000 μm$^2$.

In one aspect of the present invention, wherein the bulk acoustic wave generation region of said UHF bulk acoustic wave resonator has a side length of about 30-500 μm, preferably about 40-300 μm, most preferably about 50-200 μm, which is corresponding to a side length (the distance from the upstream end to the downstream release point) of the vortex channel of about 30-500 μm, preferably about 40-300 μm, most preferably about 50-200 μm.

In one aspect of the present invention, wherein said inlet comprises a sample inlet and an auxiliary solution inlet provided on one or both sides of said sample inlet. Based on sheath flow effect, the auxiliary solution (solution enters from the auxiliary solution inlet) may be used to control the direction and extent of flow of the sample liquid in the microfluidic channel such that the sample liquid flows through the bulk acoustic wave generating region of said UHF bulk acoustic wave resonator. The direction and extent of flow of the sample liquid in the microfluidic channel can be controlled, for example, by controlling the flow rate and inflow area of the auxiliary solution.

In one aspect of the present invention, the microfluidic system in the foregoing method is provided with a plurality of UHF resonators having the same bulk acoustic wave generation area. For example, said plurality of UHF resonators have the same release point of the bulk acoustic wave generation region or their bulk acoustic wave generation regions have the same shape. This allows cells or vesicles, or biomolecules such as nucleic acids or proteins, that have undergone undesired detachment in the upstream UHF resonator bulk acoustic wave generation region to be collected and moved in the specified direction again, so as to increase the efficiency of separation.

In one aspect of the present invention, the microfluidic system in the aforementioned method divides said fluid channel into different regions, and UHF resonators for separating different cells or vesicles are provided in the different regions. For example, in said different regions for separating different cells or vesicles, said UHF resonators may have different shapes of acoustic wave generation areas, or bulk acoustic waves of different power are generated, or have different flow rates. Thus, it can be used to separate different cells or vesicles in a solution; into different flow channels or outlets.

In one aspect of the present invention, the foregoing method can be used to separate (or isolate) different kinds or different properties (e.g., different sizes or densities, etc.) of flexible particles such as cells or vesicles, or biological macromolecules such as nucleic acids or proteins. In yet another aspect of the present invention, the foregoing method may be used to separate (or isolate) leukocytes and erythrocytes from blood, such as separating (or isolating) nucleated erythrocytes. In yet another aspect of the present invention, the foregoing method may be used to separate (or isolate) trophoblast cells from blood. In a further aspect of the present invention, the foregoing method may be used to isolate CTCs from a sample. In one aspect of the present invention, the foregoing method may be used to isolate bacteria, in particular pathogens, from a solution, or to isolate (or separate) different bacteria, from particular pathogens.

In yet another aspect of the present invention, different flexible particles such as cells or vesicles, or biological macromolecules such as nucleic acids or proteins, may be separated (or isolated) optionally by one of the following means or any combination thereof.

(a) adjusting the power of the bulk acoustic wave;
(b) Regulation of the time of generating the bulk acoustic wave;
(c) adjusting the rate of flow of the solution through the region of the bulk acoustic wave.

In one aspect of the present invention, said method further comprises increasing the power of the bulk acoustic wave generated by the UHF resonator to disrupt the cell membrane or vesicle membrane to release intracellular or vesicle material, such as proteins or nucleic acids, etc.

In one aspect of the present invention, the solution in said method is a liquid containing the cells or vesicles to be isolated, such as body fluid, whole blood, any blood fraction containing cells, tumor fragments, tumor cell suspensions, cell cultures, or culture supernatants. In yet another aspect of the present invention, said solution is blood, including whole blood or diluted blood.

In the present invention, said cells are eukaryotic animal cells, preferably mammalian cells, more preferably human cells.

The present invention also provides microfluidic devices for controlling the movement of flexible particles such as cells or vesicles, or biological macromolecules such as nucleic acids or proteins or polysaccharides in solution. Said microfluidic device may be used to obtain or purify the desired cells or biomolecules. Said microfluidic device may also be used to purify a solution (e.g. blood), for example by separating and removing cells or vesicles from the solution to obtain a purified liquid cleared of said cells or vesicles (e.g. plasma with blood cells removed). The microfluidic device provided by the present invention is used to process biologically active cells or molecules and therefore has a setup or material for handling biologically active substances. For example, the inner surface of its flow channel may be made of biocompatible materials. Another example is that it has a design that prevents cross-contamination.

In one aspect of the present invention, providing a microfluidic device for controlling the movement of target flexible particles such as cells or cellular microvesicles or biomolecular particles such as nucleic acids and proteins in a solution, comprising:

a fluid channel having an inlet and an outlet;
one or more ultra-high frequency bulk acoustic wave resonators provided on a wall of said fluid channel, said ultra-high frequency bulk acoustic wave resonators being capable of generating bulk acoustic waves with a frequency of about 0.5-50 GHz in said fluid channel and transmitted to the opposite side of said fluid channel;
a power adjusting device which adjusts the power of said bulk acoustic waves generated by said UHF resonator;
a flow rate adjusting device which adjusts the velocity of said solution flowing through the region of the bulk acoustic wave,
said UHF resonator is able to emit a bulk acoustic wave transmitted to said wall on the opposite side of said fluid channel, producing a vortex channel in the solution defined by the boundary of the bulk acoustic wave generating region of the UHF resonator, allowing the flexible particles in the solution enter and move along the vortex channel and leave the vortex channel at a set position, which is called the release point.

In one aspect of the present invention, there is a turn or curvature change in the boundary of the bulk acoustic wave generation region corresponding to said release point.

In one aspect of the present invention, said boundary line of the bulk acoustic wave generation region of said UHF resonator are set to be suitable for keeping the target flexible particles in the vortex channel while moving down along the vortex channel to the release point, for example by reducing the presence of turn or the degree of the curvature change in the boundary line of the bulk acoustic wave generation region.

In one aspect of the present invention, the angle formed by the boundary line of the bulk acoustic wave generation region of said UHF resonator and the fluid channel is set as such that the flexible particles remain in the vortex channel while moving to the release point, for example, the angle formed by the boundary line of the bulk acoustic wave generation region of said UHF resonator and the fluid channel is smaller.

In one aspect of the present invention, the bulk acoustic wave action region of the ultra-high frequency bulk acoustic wave resonator comprises a focusing zone and a sieving zone, said focusing zone being located upstream of the bulk acoustic wave action region and said sieving zone being located downstream of the bulk acoustic wave action region, wherein the setting of the bulk acoustic wave action region of the focusing zone is more suitable for keeping the flexible particles moving in the vortex channel than that of the sieving zone. In yet another aspect of the present invention, the angle between the boundary line of the bulk acoustic wave effecting region and the fluid channel in the focusing zone is smaller than that in the sieving zone. In yet another aspect of the present invention, the velocity of the flow passing through the bulk acoustic wave generation region in the focusing zone is smaller than that in the sieving zone.

In one aspect of the present invention, said power adjusting device outputs power of about 20-5000 mW, preferably 50-2000 mW, more preferably 100-1500 mW.

In one aspect of the present invention, said flow rate adjusting device adjusts the velocity of flow of said solution through the bulk acoustic region to be about 0.01-10 mm/s, preferably about 0.3-5 mm/s, more preferably about 0.5-3 mm/s.

In one aspect of the present invention, said flow rate adjusting device adjusts the velocity of flow of said solution through the bulk acoustic region to be about 0.01-100 µL/min, preferably about 0.1-50 µL/min more preferably about 0.5-30 µL/min.

In one aspect of the present invention, said fluid channel of said microfluidic device has a height of about 20-200 um, preferably about 25-100 um, more preferably about 30-80 um, for example about 40-60 um.

In one aspect of the present invention, wherein the bulk acoustic wave generation region of said UHF bulk acoustic wave resonator has a side length of about 30-500 µm, preferably about 40-300 µm, most preferably about 50-200 µm.

In one aspect of the present invention, wherein said fluidic channel has at least two outflow channels, one of which is an outflow channel for said target flexible particles being controlled to move, referred to as a particle outflow channel, and the other is an outflow channel for a solution lack of or containing less of said target cells or vesicles being controlled to move, i.e. a solution outflow channel.

In one aspect of the present invention, the microfluidic device is provided with a plurality of UHF resonators having the same bulk acoustic wave generation area.

In one aspect of the present invention, said fluidic channel is divided into different regions with UHF resonators for separating different flexible particles. For example, in said different regions for separating different cells or vesicles, said UHF resonators for separating different flexible particles may have differently shaped acoustic wave generation regions. Or, for example, in said different regions for separating different cells or vesicles, bulk acoustic waves of different power are generated, or said different regions have different flow rates.

In one aspect of the present invention, wherein said UHF bulk acoustic wave resonator is a thin film bulk acoustic wave resonator or a solid state assembly type resonator, such as a thickness stretching vibration mode acoustic wave resonator.

In one aspect of the present invention, wherein the thickness of the piezoelectric layer of the UHF bulk acoustic wave resonator of said apparatus ranges from 1 nm to 2 um.

REFERENCE SIGN OF THE DRAWINGS

100 Microfluidic device 101 Fluid channel 200 Chip housing 201 Coulter cell counter 202 UHF bulk acoustic wave resonator 203 Top electrode layer 204 Piezoelectric layer 205 Bottom electrode layer 206 Acoustic reflection layer Acoustic impedance layer 207 Bottom liner layer 208 Top 300 PCL controller 301 High frequency signal generator 302 Power amplifier 303 Impedance meter 400 Liquid injection and flow rate regulation device 500 Acoustic jet 501 Vortex 600 Larger size particles 601 Medium size particles 602 Smaller size particles

BRIEF DESCRIPTION OF THE DRAWINGS

In order to more clearly illustrate the technical solutions in the embodiments or prior art of the present invention, the following is a brief description of the accompanying drawings for use in the description of the embodiments or prior art. It will be apparent that the accompanying drawings in the following description are some embodiments of the present invention, and that other drawings of the present invention are available to a person of ordinary skill in the art.

FIG. 3(a) shows images of the motion trajectories of individual Hela cells in the vortex channel formed by the bulk acoustic waves generated by the UHF bulk acoustic wave resonator of the microfluidic device system (superimposed trajectories of individual cells at different times); FIG. 3(b) shows a schematic diagram of the motion trajectories of Hela cells (superimposed trajectories of multiple cells) and an analysis graph; FIG. 3(c) shows a time and velocity analysis graph of Hela cells.

FIG. 4(a) shows images of cell movement in the vortex; FIG. 4(b) shows cell settling after stopping the bulk acoustic wave; and FIG. 4(c) shows the arrangement of cells in the vortex tunnel.

FIGS. 5(c) and 5(d) show photographs of Hela cells being captured and blood cells being released in two microfluidic channel setups, and FIGS. 5(a) and 5(b) are an analysis and schematic diagrams of FIGS. 5(c) and 5(d), respectively. FIG. 5(e) shows the distribution of hemocytes upstream and downstream of the bulk acoustic wave action region (color line in FIGS. 5(c) and (d)).

DETAILED DESCRIPTION

The nature and benefits of the present disclosure are further described with reference to the following examples, which are intended to illustrate the invention provided herein and not to limit the scope of the present disclosure.

Example 1 Experimental Method and Materials

Microfluidic Channel and UHF Bulk Acoustic Resonator Preparation:

Microfluidic channels made of polydimethylsiloxane (PDMS) were prepared by soft lithography.

The bulk acoustic wave resonator devices are prepared by chemical vapor deposition, metal sputtering, and lithography on a silicon wafer. The specific methods are as follows.

1. The surface of the silicon wafer is thoroughly cleaned using a solution with a 3:1 volume ratio of concentrated sulfuric acid to hydrogen peroxide, which effectively removes organic and inorganic materials from the wafer.

2. On the cleaned silicon wafer, an aluminum nitride film is formed by surface sputtering, and then a silicon dioxide film is deposited using an ion-enhanced chemical vapor deposition method. Then, using the same method, the aluminum nitride film and the silicon dioxide film are deposited alternately to form a Bragg acoustic reflection structure with alternating layers of aluminum nitride and silicon dioxide.

3. On top of the Bragg reflector structure, a 600 nm molybdenum film is sputtered as the bottom electrode. Next, the molybdenum electrode film is photolithographed using standard photolithography techniques, including glue coating, exposure, and development, followed by etching to form a bottom electrode with a target pattern.

4. Another layer of aluminum nitride film is sputtered on the molybdenum electrode as a piezoelectric layer. The pattern is defined on the aluminum nitride film using dry etching.

5. The pattern on the mask plate is transferred using negative photoresist and then a 50 nm thick layer of titanium tungsten alloy is sputtered, which acts as an adhesion layer to increase the adhesion of the gold electrode. After that, a 300 nm thick layer of gold thin film of the upper electrode is formed by using vapor deposition. Finally, acetone is used to remove the gold film around the target pattern to form the gold electrode with the target pattern.

Finally, the bulk acoustic wave resonator device is integrated with the PDMS microchannel chip. The bulk acoustic wave resonator device is set in the middle of the channel.

The bulk acoustic wave resonator device is connected to a network analyzer using a standard SMA interface, and the frequency of the bulk acoustic wave emitted by the bulk acoustic wave resonator device in the microchannel can be measured by testing the spectrum to find the resonance peak.

Instruments and Materials

Signal generator: MXG Analog Signal Generator, Agilent, N5181A 100 kHz-3 GHz.

Power amplifier: Mini-Circuits, with 35 dBm enhancement of the original RF source power Syringe Pump: New Era Pump Systems, Inc., NE-1000 Cells.

Hela cell line: ATCC #CCL2, Guangzhou Genealogy Biotechnology Co.

Cell culture: Hela cells were cultured in DMEM medium (Thermo) supplemented with 10% FBS (Thermo), 100 U/ml penicillin (Thermo) and 100 ug/ml streptomycin (Thermo). The cell densities in culture ranged from $1 \times 10^5$/mL to $2 \times 10^6$/mL. For microfluidic experiments, dilution to $1 \times 10^5$/mL was used for experiments. PBS buffer (Gibco).

Cell or Tumor Markers or Stains.

Calcein-AM (Beijing Solaibao Technology Co., Ltd., China)

Anti-EpCAM (Biolegend, USA)

4',6-diamidino-2-phenylindole (DAPI) (Invitrogen, USA)

Example 2

In this embodiment of the present invention, a microfluidic device is provided which can be used to separate and capture flexible particles in solution, in particular flexible particles with a diameter of about 0.2-30 um. The flexible particles may be artificial or natural, and typically said particles are microclusters with a membrane structure, in particular microclusters with a lipid bilayer or a lipid-like bilayer. The flexible particles covered by the present invention typically have a diameter of about 0.2-30 um. The flexible particles suitable for processing by the present invention are typically about 0.8-25 um in diameter, preferably about 1-20 um in diameter.

The method and devices of the present invention can be used to separate flexible particles in solution, for example in blood to separate blood cells and obtain purified plasma.

Figure 1:
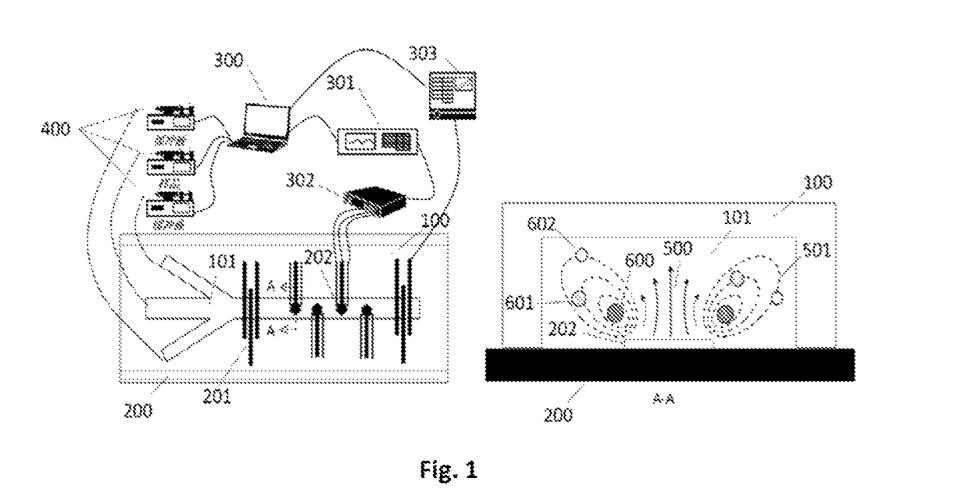
FIG. 1 Schematic diagram of the structure of a microfluidic device system of an embodiment of the present application.

As shown in FIG. 1, said microfluidic device 100 includes a fluid channel 101, a UHF bulk acoustic wave resonator 202, a bulk acoustic wave power regulation device, and a liquid injection and flow rate adjusting device 400.

The microfluidic device provided by the present invention may be provided independently or may be part of a microfluidic system, for example in the form of a loadable chip. Microfluidic systems or devices can be used to contain and transport fluidic materials such as liquids with flow channel sizes in the micron or even nanometer range. Typical microfluidic systems and devices typically include structures and functional units of millimeter or smaller size.

The fluid channels, or microfluidic channels, of said microfluidic devices are generally closed except for openings for fluid entry and exit. The cross section of the fluid channel typically has dimensions of 0.1-500 m, which can be of various shapes including elliptical, rectangular, square, triangular, circular, etc. Fluid channels can be prepared using a variety of known micropreparation techniques with materials including, but not limited to, silica, silicon, quartz, glass, or polymeric materials (e.g., PDMS, plastic, etc.). Said channels can be coated with a coating. The coating may modify the properties of the channel and may be patterned. For example, the coating may be hydrophilic, hydrophobic, magnetic, conductive, or biologically functionalized.

In one aspect of the present invention, said fluid channels of the microfluidic device have a height of about 20-200 μm, preferably about 25-100 μm, more preferably about 30-80 μm, for example about 40-60 μm.

In one aspect of the present invention, said fluid channel of the microfluidic device has a width of about 50-1000 μm, preferably about 100-500 μm, more preferably about 150-300 μm.

The microfluidic channel 100 in this embodiment has an inlet and an outlet for solution entry and exit. Said inlet is connected to a fluid injection device for receiving the solution. Said inlet in this embodiment comprises a sample inlet 101 and a buffer inlet 102, wherein said buffer inlet is two inlets provided on either side of said sample inlet. Said microfluidic inlet setting facilitates passive focusing of the sample solution when passing through the sample inlet in the middle by this setting (sample flow in the middle and buffer flow on both sides).

As shown in FIG. 1, the microfluidic device of this embodiment includes a liquid injection and flow rate adjustment device 400 for controlling the solution injection and controlling the flow rate of the solution. Said solution may be a solution containing a sample. For example, said sample is a solution containing cells to be captured. Said sample may comprise body fluids, whole blood, any blood fractions containing cells, tumor fragments, tumor cell suspensions, cell cultures or culture supernatants, etc. Said solution may be a variety of body fluids, including blood, tissue fluid, extracellular fluid, lymphatic fluid, cerebrospinal fluid, room water, urine, sweat, etc.

The flow rate of the injected solution can be controlled by means of an external pressure source, an internal pressure source, electrodynamics, or magnetic field dynamics. The external pressure source and internal pressure source can be a pump, such as a peristaltic pump, a syringe pump, or a pneumatic pump. In this embodiment, a syringe pump fine-tuned by a computer is used to control the flow rate of the liquid injection.

In the present invention, the flow rate of the solution ranges from about 0.1-10 mm/s, preferably from about 0.3-5 mm/s, more preferably from about 0.5-3 mm/s. In another aspect of the present invention, the flow rate of said solution ranges from about 0.1-100 μL/min, preferably from about 0.1-50 μL/min, more preferably from about 0.5-30 μL/min.

Said channels may be a single channel, or a plurality of channels arranged in parallel, wherein the outflow and inflow of solution and the flow rate thereof of each channel may be controlled jointly or independently as desired.

The microfluidic device of the present invention has one or more UHF bulk acoustic resonators 200, which are provided on one of the walls of the fluid channel (typically provided at the bottom of the flow channel). Said UHF bulk acoustic wave resonators may generate bulk acoustic waves at a frequency of about 0.5-50 GHz in said fluid channel which transmit to a wall on the opposite side of said fluid channel (typically the top of the flow channel).

The UHF bulk acoustic wave resonator that may be used in the present invention may be a thin film bulk acoustic wave resonator or a solid state assembly type resonator, such as a thickness stretching vibration mode acoustic wave resonator.

As shown in FIG. 1, the microfluidic device of this embodiment has a plurality of UHF bulk acoustic wave resonators 202 disposed at the bottom of the flow channel.

Said UHF bulk acoustic wave resonators are bulk acoustic wave generating components that can generate bulk acoustic waves in said fluid channel that are transmitted to the opposite side of said fluid channel's wall. Said UHF resonator can emit bulk acoustic waves transmitted to the opposite wall of said fluid channel, generating a vortex channel in the solution defined by the boundary of the bulk acoustic wave generating region of the UHF resonator, where cells or vesicles in the solution enter the vortex channel and move along the vortex channel and leave the vortex channel at a set position, which is called the release point.

Figure 2:
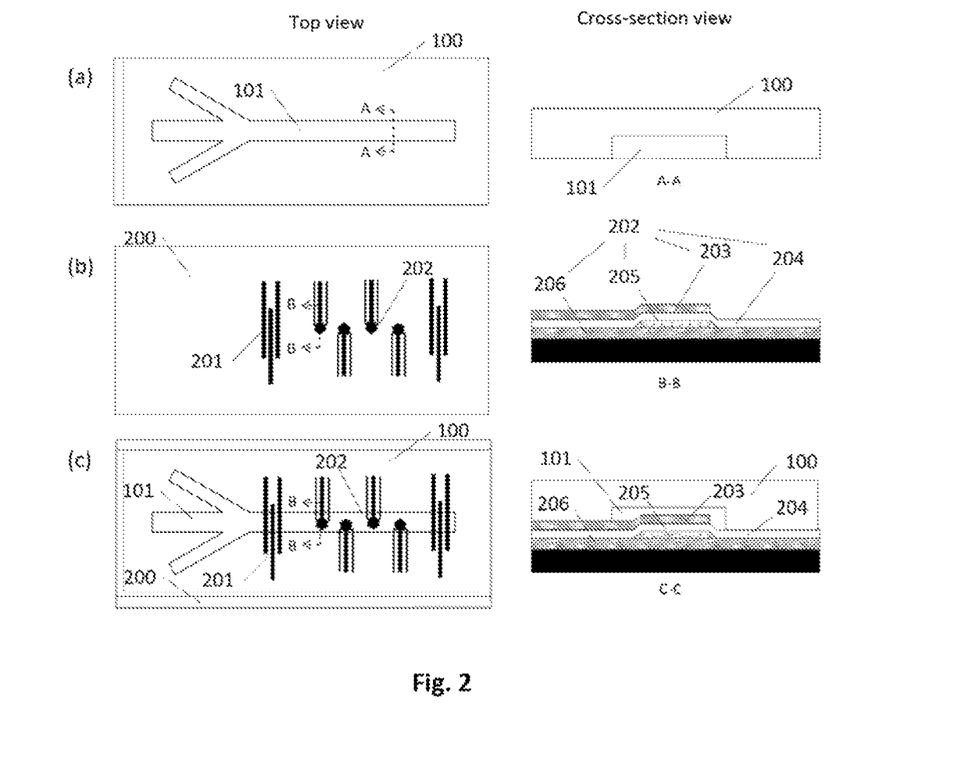
FIG. 2 Schematic diagram of the structure of a UHF bulk acoustic wave resonator in a microfluidic device system of an embodiment of the present application; wherein, (a) represents a top view (left) and an A-A section (right) of the microfluidic channel of the microfluidic system shown in FIG. 1; (b) represents a top view (left) of the UHF bulk acoustic wave resonator (wherein the black pentagonal area is the acoustic wave effecting region of the UHF bulk acoustic wave resonator) and B-B cross-sectional view (right); (c) top view (left) and cross-sectional view (right) of the microfluidic channel+UHF bulk acoustic resonator.

As shown in the cross-section on the right side of FIG. 2(b), said UHF bulk acoustic wave resonator includes an acoustic wave reflector layer 206, a bottom electrode layer 205, a piezoelectric layer 204 and a top electrode layer 203 provided sequentially from the bottom to the top, said bottom electrode layer, piezoelectric layer, top electrode layer and acoustic wave reflector layer overlap each other to form a bulk acoustic wave generation region. As shown in the top view on the left side of FIG. 2(b), the top surface of said UHF bulk acoustic wave resonator is configured on the wall of the fluid channel to generate bulk acoustic waves emitted in a direction perpendicular to said wall to the opposite wall; in general, the area constituted by the top surface of the UHF bulk acoustic wave resonator is the bulk acoustic wave generation region, also referred to as the bulk acoustic wave region or the bulk acoustic wave effecting region in this specification. In one aspect of the present invention, said bulk acoustic wave action region has an area of about 500-200,000 μm$^2$, preferably about 5,000-50,000 μm$^2$, and most preferably about 10,000-25,000 μm$^2$. The bulk acoustic wave action region of this embodiment, as shown in FIG. 2, is pentagonal in shape with sides of about 120 micrometers. The successive vortex generated by the UHF bulk acoustic waves in the solution forms an acoustic fluid vortex channel. Since the vortex is generated by the volume force caused by the attenuation of acoustic wave in the solution, the central axis of the vortex is above the boundary of the bulk acoustic wave action, the shape of the vortex channel is essentially the same as the shape of the bulk acoustic wave action region and the vortex channel is located above the boundary of the bulk acoustic wave action region.

In the present invention, said shape of the bulk acoustic wave action region includes at least, but is not limited to, one of the following: a circle, an ellipse, a semicircle, a parabola, a polygon with an acute or obtuse angle at the vertex, a polygon with the vertex replaced by a circular arc, a polygon with any combination of an acute angle, a semicircle or a parabola at the vertex, or a repeatedly arranged square or circular array of the same shape. The present application provides the acoustic action area of the above-mentioned shapes, but other acoustic action areas of any shape are also within the scope of protection of the present application. In the present invention, a preferred shape of the bulk acoustic wave generation region of a UHF resonator is spindle-shaped.

In one aspect of the present invention, the boundary lines of the bulk acoustic wave generation region of the UHF resonator described above (i.e., the shape of the corresponding vortex channel) are set to be suitable for cells or vesicles in the vortex channel to move along the vortex channel to the release point. This prevents the cell or vesicle from leaving the vortex channel and thus prevents the cell or vesicle from leaving the vortex channel not from the release point as set.

In yet another aspect of the present invention, the cell or vesicle is kept in the vortex channel till moving to the release point by adjusting the shape of the boundary lines of the bulk acoustic wave generation region of said UHF resonator. As previously mentioned, the presence of turns or curvature changes in the boundary lines of the bulk acoustic wave generation region may increase the chance that the cell or vesicle break away from the vortex channel. Therefore, the cells or vesicles may be kept moving in the vortex channel by reducing the presence of turns or curvature changes in the boundary lines of the bulk acoustic wave generation region, i.e., reducing the number of cells or vesicles detached from the vortex channel and improving the efficiency of separation.

In yet another aspect of the present invention, the cells or vesicles are kept in the vortex channel till moving to the release point by adjusting the angle formed between the boundary line of the bulk acoustic wave effecting region and the fluid channel. The inventor unexpectedly found that the smaller the angle formed between the boundary line of the bulk acoustic wave effecting region and the fluid channel, the easier it is to keep the cells or vesicles moving in the vortex channel, so that fewer cells or vesicles detach from the vortex channel and thus improving the efficiency of separation.

In yet another aspect of the present invention, the bulk acoustic wave effecting region of the UHF bulk acoustic wave resonator in the microfluidic system has a focusing zone and a sieving zone. The focusing zone is located upstream of the bulk acoustic wave effecting region (i.e., near the direction of sample inflow and away from the release point), and the sieving zone is located downstream of the bulk acoustic wave action region (i.e., near the direction of sample outflow; nearer to or including the release point). The setup of the bulk acoustic wave effecting region in the focusing zone is more suitable to keep the flexible particles moving in the vortex channel compared to that of the sieving zone: cells or vesicles in the vortex channel in the focusing zone move along the same or similar direction as the flow direction and are subject to relatively less vortex dragging force, making it easier for the cells or vesicles to enter and remain in the vortex channel; in the downstream sieving zone, cells focused to the vortex center can move more stably along the vortex channel than unfocused cells. In yet another aspect of the present invention, the angle formed between the boundary line of the bulk acoustic wave effecting region and the fluid channel in the focusing zone is smaller than that in the sieving zone. For example, in the focus zone, the boundary of the bulk acoustic wave effecting region and the fluid channel direction is the same or basically the same (for example, the angle is less than 10°); the cells in this region of the vortex channel being effected by the vortex drag force which basically does not change the cell movement direction (i.e., the direction of the flow) but only let the cell move to the center of the vortex, thus achieve the focus of the cell; in sieve zone, angle between the boundary of the bulk acoustic wave effecting region and the fluid channel is bigger, the cells focused to the vortex center moves more stably in the vortex channel than the unfocused cells. In yet another aspect of the present invention, the velocity of the fluid flow through the bulk acoustic wave effecting region in the focusing zone is controlled to be less than the velocity of the fluid flow through the bulk acoustic wave effecting region in the sieving zone.

The fluid channels of this embodiment have a plurality of UHF bulk acoustic wave resonators, as shown in the right-hand section of FIG. 2. In one aspect of the present invention, they are arranged in a straight line in the same direction as the direction of fluid motion.

The UHF bulk acoustic wave resonator employed in this embodiment of the present invention is a thickness-stretching vibration mode in which a thin film layer of piezoelectric material is made by growing in the vertical direction and is excited by coupling the vertical electric field through the d33 piezoelectric coefficient. The UHF bulk acoustic resonator employed in the present invention can generate localized acoustic flow at the interface between the device and the liquid without a coupling medium or a coupling structure.

The UHF bulk acoustic wave resonator employed in the present invention produces a UHF bulk acoustic wave in the solution that is essentially free of standing waves. As shown in the right panel of FIG. 1, the UHF resonator emits a bulk acoustic wave transmitted to the opposite wall of said fluid channel (e.g., the top of the flow channel), and the volume force generated by the acoustic wave attenuates in the fluid and causes an acoustic jet 500 to appear in the flow-through solution, resulting in a localized three-dimensional vortex 501 of the fluid in the microfluidic channel, and the successive vortex caused by the UHF bulk acoustic wave forms an acoustic fluid vortex channel. Since the vortex is generated by the volume force triggered by the acoustic wave attenuation, the central axis of the vortex is above the boundary of the bulk acoustic wave action, so the shape of the vortex channel is basically the same as the shape of the bulk acoustic wave effecting region, located above the boundary of the bulk acoustic wave action region. The acoustic fluid vortex is caused by the nonlinearity of the acoustic wave propagation in the liquid medium. And the strength of the amplitude of the acoustic wave directly determines the strength of the acoustic fluid vortex. By adjusting the applied power, the amplitude of the acoustic wave can be regulated, which in turn controls the speed of the acoustic fluid vortex. The particles in the vortex (including larger size particles 600, medium size particles 601, smaller size particles 602) are subjected to forces including the vortex generated fluid drag force (Stokes drag force), flow layer generated inertial drag force (inertial lift force) and acoustic radiation force caused by acoustic attenuation. The magnitude of the fluid drag force is positively related to the particle such as particle diameter, while the magnitude of the acoustic radiation force is positively related to the square of the particle size. As the size of the particle increases, the main-effecting force will change from fluid drag to acoustic radiation force, which pushes the particle to the center of the vortex. Larger particles are subjected to greater acoustic radiation force and thus move to the center of the vortex; while smaller particles rotate at the periphery under the action of the vortex drag force. Particles move along and downstream of the bulk acoustic effecting region under the action of the lateral drag force generated by the now layer.

The fluid drag force and acoustic radiation force induced by the acoustic waves in the vortex channel can be deduced from certain formulae, but the inertial lift force generated by the acoustic fluid vortex (inertial lift force) can hardly be calculated, especially in the case of fluids containing complex compositions. Compared to the two-dimensional particle capture in the prior art, the method and apparatus of the present invention involve deformable cells or vesicles whose forces and trajectories in the acoustic fluid vortex and the channels formed thereof are more complex, due to the interaction between the individual vortices and the migration of particles between the vortices have an impact on capture of the particles in the fluid, especially in the presence of a large number of said cells or vesicles in the fluid; the cells or vesicles interact and influence each other due to collisions and other phenomena, and the interacting forces and motions in the vortex differ from those calculated and simulated theoretically, and the motion patterns and trajectories in the vortex channel are even more impossible to predict based on theoretical calculations and simulations.

The applicant unexpectedly found through experiments that, in the method and device of the present invention, cells or vesicles in solution passing through the region of the acoustic fluid vortex channel caused by ultra-high frequency bulk acoustic waves will enter the vortex channel and move along the vortex channel under the suitable conditions of flow velocity and bulk acoustic wave power; under the effect of lateral drag force generated by flow layer, at a certain position in the vortex channel, the cells or vesicles will leave the vortex channel and moves downstream, i.e., is released. The release point is usually located in the most downstream region of the vortex channel.

The inventors also discovered, unexpectedly, that the location where the cell or vesicle leaves the vortex channel is usually at a position where a jump point of the acoustic radiation force occurs. When the conditions such as vortex-generating bulk acoustic wave power, solution flow rate, fluid channel shape and size are fixed, the location where the cell or vesicle leaves the vortex channel is usually at a position where the vortex channel has a turn or corner. Without being bound by the theory, the applicant believes that the reason for this phenomenon is that at the turn or corner of the vortex channel, the direction of the vortex and/or the direction of acoustic radiation force suddenly change, and the larger cells or particles, which are already focused on the vortex center and subject to greater acoustic radiation force, are able to change their direction of motion with the vortex channel and quickly refocus to the center of the vortex channel after the turn; while the smaller particles or cells are more affected by the change in drag direction and easier to leave the vortex channel.

By adjusting the shape and position of the bulk acoustic wave effecting region of the UHF bulk acoustic wave resonator, the cells or vesicles in solution are caused to enter and move along the vortex channel and leave the vortex channel at a set position. Thereby said cells or vesicles leave the bulk acoustic wave action region in the specified position and direction into a desired outflow channel, such as into said particle outflow channel. This set position of leaving the vortex channel is called the release point, i.e. the position where said cell or vesicle leaves the region of bulk acoustic action. The solution excluding said cell or vesicle which is controlled to move then maintains the inflow direction into the aforementioned solution outflow channel.

Thus, the present applicant's inventors have discovered and provided methods for separation of target cells or vesicles more efficiently.

In the present invention, the frequency of the thin film bulk acoustic wave resonator is mainly determined by the thickness and material of the piezoelectric layer. The thickness of the piezoelectric layer of the thin film bulk acoustic resonator used in the present invention ranges from 1 nm to 2 um. The frequency of the UHF bulk acoustic resonator of the present invention is in the range of about 0.5-50 GHz, preferably about 1-10 GHz.

The bulk acoustic wave generated by said UHF bulk acoustic wave resonator is driven by a signal from a high frequency signal generator. The pulsed voltage signal driving the resonator can be driven with pulse width modulation, which can produce any desired waveform, such as a sine wave, square wave, sawtooth wave, or triangle wave. The pulsed voltage signal can also have an amplitude modulation or frequency modulation start/stop capability to start or eliminate bulk acoustic waves.

The microfluidic device of the present invention further comprises a power regulation device which regulates the power of the bulk acoustic waves generated by said UHF resonator. In this embodiment, said power regulating device is a power amplifier having a power regulation function. In one aspect of the present invention, said power adjusting device has an output power of about 20-5000 mW, preferably 50-2000 mW, more preferably 100-1500 mW. Due to the high energy conversion efficiency of the thin film bulk acoustic wave resonator which essentially cause no energy loss, the output power of said power adjusting device can be considered essentially as the output power of the thin film bulk acoustic wave resonator generating bulk acoustic waves in fluid. In the microfluidic device of the present invention, said power adjusting device may be connected to a high frequency signal generator. The output circuit of said power amplifier is connected to the bottom electrode, piezoelectric layer, and top electrode of said ultra-high frequency bulk acoustic wave resonator, respectively.

Example 3 Cell Movement in Vortex Channels Caused by UHF Bulk Acoustic Waves

Hela cells were dissolved in DMEM culture medium and prepared as sample solution (cell concentration of ~1*10$^5$/mL). In addition, Hela cells were labeled with Calcein-AM in order to be observed of their movement. The samples were injected from the sample inlet into the microfluidic channel.

The height of the said microfluidic channel was 50 um. The UHF bulk acoustic wave resonator frequency was 1.83 GHz and the output power was 30 mW. The sample input flow rate was controlled to be 1 uL/min and approximately 0.67 mm/s.

Figure 3:
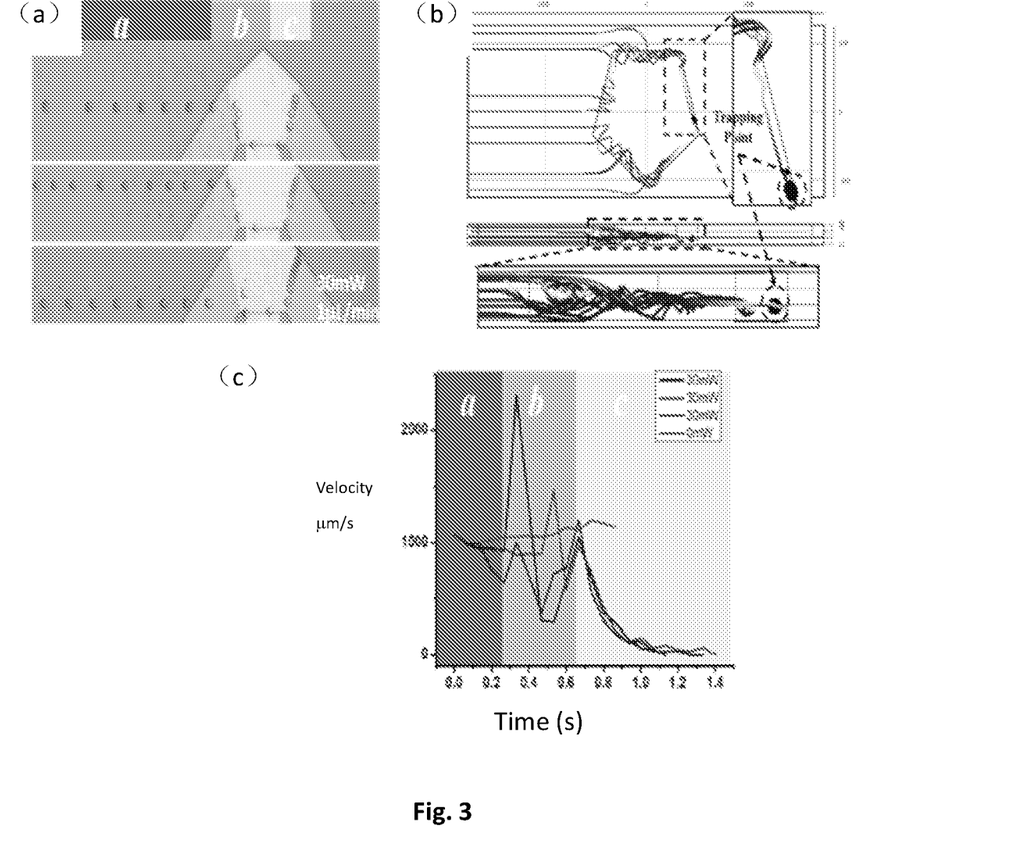
FIG. 3 shows Hela cells entering the vortex channel in one of the microfluidic device systems of an embodiment of the present application.

The results are shown in FIG. 3. FIG. 3(a) shows the motion trajectory of a single Hela cell in the vortex channel formed by the bulk acoustic wave generated by the UHF bulk acoustic wave resonator of the microfluidic device system. It is a superposition of multiple images of the same single cell at different times to show its movement trajectory. FIG. 3(b) shows the schematic diagrams of the movement trajectories of different individual cells; the top view is shown in the upper panel and the side view in the lower panel. FIG. 3(c) shows the time and velocity analysis of Hela cells.

In the microfluidic device of the present invention, the bulk acoustic waves generated by the UHF bulk acoustic wave resonator cause the solution to generate vortices. Each vortex connects to an adjacent vortex, forming an acoustic fluid vortex channel or vortex tunnel along the boundary of the acoustic wave effecting region of the UHF bulk acoustic wave resonator. The combined effect of multiple vortices and the interaction between vortex and laminar flow causes the cells entering the vortex channel and move along the vortex channel, and the cells are floating above the bottom of the microfluidic channel with no contact with the microfluidic channel.

The image sequence in FIG. 3(a) demonstrates the moving trajectory of a single HeLa cell. The movement process can be divided into three phases occurring in regions a-b-c, as shown in FIG. 3(a) and FIG. 3(c). In region a, the cells move at a uniform velocity in the lateral flow. In region b, the direction of cell movement is changed by the vortexes. The cells enter the vortex tunnel generated by the acoustic waves and move along the vortex tunnel while focused on the 3-D axis of the tunnel. Cells with different initial positions have varying velocities as they enter the vortex array. Due to the difference in orientation relative to the vortex, cells with initial positions in the lower layers of the microchannel accelerate, while cells with initial positions in the upper layers slow down. The speed of cell movement gradually slows down in region c. Due to the tuning of the cell trajectory in the vortex tunnel, the process of cell deceleration and movement has good stability, and the cells with different entry initial positions have good consistency of deceleration and movement.

FIG. 3(b) schematic diagram further illustrates the movement of cells in the flow channel under the action of bulk acoustic waves. FIG. 3(b) is a superimposed schematic of the motion trajectories of different individual cells. The top view of FIG. 3(b) shows the top view and the bottom view shows the side view. From the top view perspective, it can be seen that the trajectories of the cells are distributed only at the boundary of the acoustic wave effecting region of the UHF bulk acoustic resonator. From the side view perspective, it can be seen that the cells all float above the bottom of the channel and have no contact with the bottom.

Experimental and simulated calculations revealed that the forces and motions of the cells in the fluid, especially in the vortex, differed from the theoretical values derived from the simulated equations. It is hard to be predicted. Cells have mechanical properties that are significantly different from, for example, polystyrene particles, such as inertness, rigidity, and complex structures with multiple substances. In the context of acoustic wave dynamics and vortex hydrodynamics, for simulated and theoretical calculation of the motion of an object in a vortex, the difference in density and speed of sound of the object relative to the solution medium am very important factors. Moreover, the deformation of the cell by the acoustic and drag forces makes the combined force exerted by the vortex on the cells significantly unpredictable.

Example 4 Cell Suspension and Settling in a Microfluidic Channel

In prior art acoustic vortex methods, the motion of particles or cells in the z-axis of the microfluidic channel (i.e., the vertical direction of the flow channel) is ignored because in-plane acoustic flow is the dominant flow. However, the trajectory of the i-axis is important for single-cell operation and high-precision detection. Due to the unique TE vibration mode of the UHF bulk acoustic wave employed in the present invention, the dominant flow in the microfluidic system of the present invention is out-of-plane (out-of-plane). To better investigate the vortex tunneling generated by UHF bulk acoustic waves in the microfluidic system of the present invention, Calcein-AM-labeled Hela cells were used to observe and measure the cell motion in the z-axis using a confocal microscope (Leica, Germany). To capture the particle trajectories within the vortex tunneling, the x-z-t mode was used. In this mode, the capture speed is 37 frames per second.

The same experimental setup is similar with that in Example 3, except that the input flow rate of the sample containing Hela cells is reduced to 0.1 L/min. After the sample containing cells and the buffer were input into the microfluidic channel, the signal generator was turned on and the cells were captured in the acoustic action region. Then the pressures in inlet and outlet are adjusted to the same and the fluid is stagnant. The motion of the cells in the vortex is observed. Then the signal generator is turned off and the motion of the cells is observed.

Figure 4:
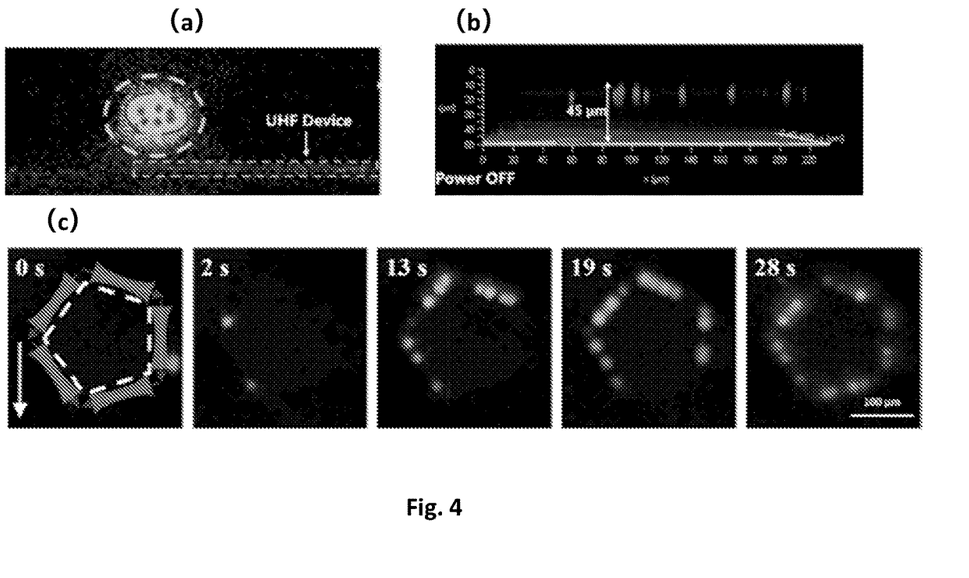
FIG. 4 shows the movement of cells in a vortex channel in a microfluidic device system of an embodiment of the present application.

The results are shown in FIG. 4. FIG. 4(a) shows the images of cell movement in the vortex, which is a composite stacked image (6 images, 27 ms apart), where the red dots show the center of the particles in each frame, the green dashed circles indicate the range particle motion and the red arrows indicate the direction of particle motion. When the signal generator power is turned on, bulk acoustic waves are generated and form vortices and vortex tunnels within the flow channel, and the particles are relatively "stationary" suspended at a distance from the chip surface. As shown in FIG. 4(b), when the power is turned off, the bulk acoustic wave disappears and the particle settles to the chip surface under the combined effect of gravity and buoyancy. The results show that the particles are indeed trapped in the vortex tunnel.

FIG. 4(c) shows that the Calcein-AM-labeled Hela cells are trapped in the vortex tunnel. The tunnel has the same shape as the boundary of the acoustic wave generating region of the UHF bulk acoustic wave resonator.

Example 5 Isolation of Different Cells from Whole Blood

In the blood environment, cells have viability and intact function, which is important for biological studies. e.g., cell metabolism, proteomics. However, whole blood is a more challenging sample to work with than diluted blood samples. In terms of physical parameters, whole blood is more viscous and turbid, both of which can have a serious negative impact on cell manipulation. Physical fields, such as dielectric fields, magnetic fields, and hydrodynamic fields, are disordered in blood samples. In addition, high densities of cells, especially erythrocytes ($10^9$/mL), can cause strong interactions between cells, which can alter the trajectory of the specimen and affect the stability of cell motility.

The inventors demonstrated that the apparatus and method of the present invention are capable of selectively controlling and isolating target cells in whole blood.

Hela cells are dissolved in DMEM culture medium and mixed with whole blood to prepare a test sample solution (Hela cell concentration is adjusted to approximately $1 \times 10^5$ cells/mL).

The sample was injected from the sample inlet into the microfluidic channel. PBS buffer is injected into the microfluidic channel from the buffer inlets on both sides of the sample inlet. PBS acts as a sheath flow and serves to ensure the lateral extent of the sample fluid, ensuring that all samples will pass over the UHF bulk acoustic wave resonator set in the mid of the channel.

Figure 5:
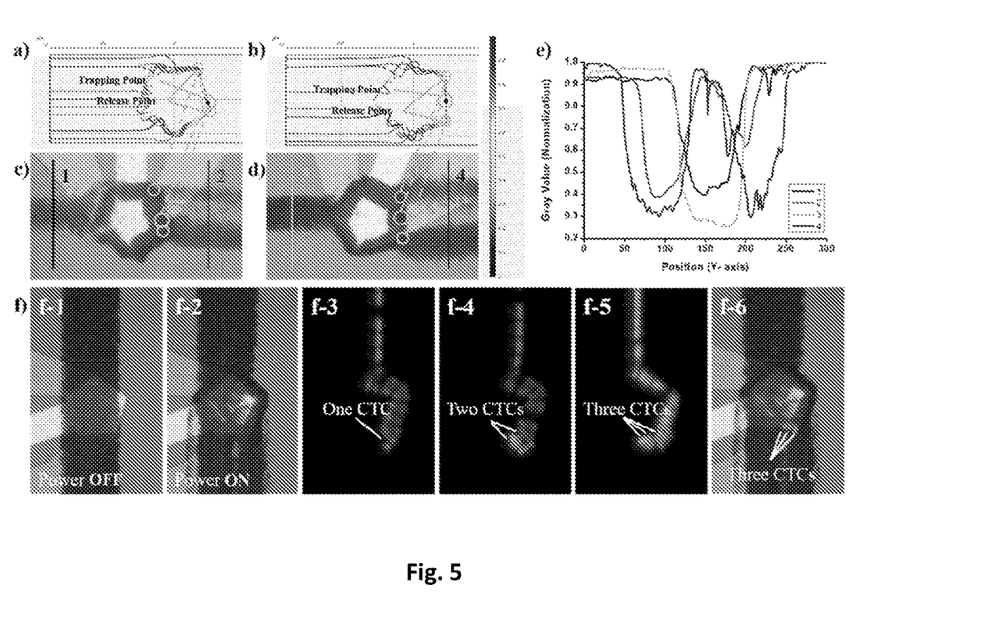
FIG. 5 shows that a microfluidic device system of an embodiment of the present application is capable of isolating and capturing Hela cells from a mixture of whole blood.

The results are shown in FIG. 5, where Hela cells in whole blood are selectively caused to enter the vortex channel and move along within the vortex channel.

FIGS. 5(*c*) and 5(*d*) show the photographs of Hela cells entering the vortex channel while blood cells passing through the bulk acoustic wave region under the two microfluidic channel setups, and FIGS. 5(*a*) and 5(*b*) are the analysis and schematic diagrams of FIGS. 5(*c*) and 5(*d*), respectively. In this embodiment, the bulk acoustic wave effecting region of the UHF bulk acoustic wave resonator is pentagonal. In FIG. 5(*c*), the bulk acoustic wave effecting region is set to have a protruding point (one corner of the pentagon) downstream of the liquid inflow direction: the positions where the blood cells leave the bulk acoustic wave effecting region is near said corner of the pentagon. In FIG. 5(*d*) the bulk acoustic wave action region is adjusted to have one of the corners of the pentagon placed along the midline of the flow channel and opposite to the direction of fluid inflow into the channel; the releasing points of the blood cells, are located at the two end points of the downstream side line of the pentagon. FIG. 5(*e*) shows the distribution of blood cells upstream and downstream of the region of bulk acoustic wave action (regions separated by the lines in the photos in FIGS. 5(*c*) and 5(*d*)). The curves indicate that the blood cells are released evenly at two symmetric release points. FIG. 5(*f*-1) shows that the three-phase flow input setting: the injected sample solution in the middle is passively focused by the two PBS solution at both sides, allowing better sample flow through the acoustic effecting region of the high-frequency bulk acoustic resonator. FIG. 5(*f*-2) shows the flow of blood cells when the power is turned on and bulk acoustic waves are generated within the microfluidic channel. FIGS. 5(*f*-3)-5(*f*-5) show CTCs being selectively caused to enter into the vortex tunnel: the composite stacked image sequence demonstrates the CTCs motion trajectory. FIG. 5(*f*-6) shows the results of selective CTC entry into the vortex tunnel: the merged images show that the device provided by the present invention allowing CTCs' selectively entry and stably retained in the vortex tunnel, while allowing the releasing of blood cells.

The release point of the blood cells is the jump point of vortex and acoustic radiation force. In the case where the device is a positive pentagon, the cells are focused in the vortex tunnel, and since each edge of the tunnel is straight, the laminar flow generates a lateral drag force moving downstream, the vortex drag force makes the focused cells do not easily leave the vortexes while moving along the boundary. At the corners, the vortex direction and the direction of acoustic radiation force both change abruptly, and the larger cells, which are already focused on the vortex center and subject to greater acoustic radiation force, are able to change their direction of motion with the vortex and refocus quickly to the vortex center on the new side; while the smaller cells are dislodged from the tunnel due to the dominant laminar drag force. By adjusting the area of bulk acoustic wave action of a microfluidic device, such as an UHF bulk acoustic wave resonator, non-target cells are carried away by the laminar flow, only the target cells are able to enter and/or remain in the vortex channel.

Example 6 Effect of Different UHF Bulk Acoustic Wave Resonator Settings on the Separation of Blood Cells from Whole Blood This experiment tests the effect of separating blood cells from plasma in whole blood using the microfluidic system and method of the present invention.

Figure 6:
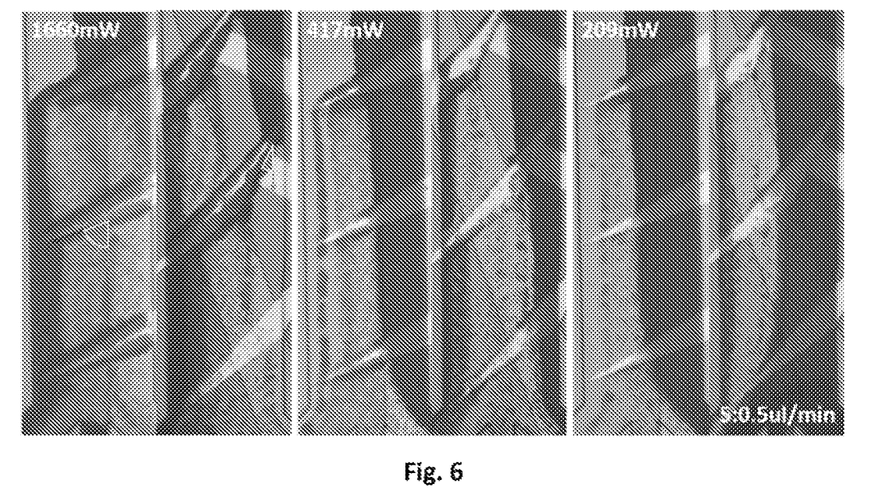
FIG. 6 shows the effect of different UHF bulk acoustic wave resonator settings on the separation of blood cells in whole blood.

Microfluidic channels as shown in FIG. 6 were prepared and constructed according to the method described in Examples 1 and 2. Each of these microfluidic channels has three sequentially arranged UHF resonators with the same bulk acoustic wave generation region. The use of multiple UHF resonators in the flow channel direction enhances the control of same target particles. The surface of the UHF resonators (i.e., the bulk acoustic wave generation region, shown as a triangular device in the Figure) is located on one side of the microfluidic channel (right side of the Figure), and the microfluidic channel is set up with two solution inlets. Whole blood sample is input through the right side inlet. PBS solution is input through the left side inlet. The blood sample flow is fully passed through the bulk acoustic wave generation region by adjusting the flow of PBS solution and the focusing effect of sheath flow. The downstream corner of the triangular bulk acoustic wave generation region (i.e., the vortex channel) is the target cell release point, and the released cells leave the downstream corner position and enter the cell outflow channel (the channel on the left at the bottom of the Figure) in the direction of the microfluidic channel.

The height of the microfluidic channel described is 50 um. The UHF bulk acoustic wave resonator frequency is 1.83 GHz, and the three powers of the acoustic wave are as shown in FIG. 6. The sample flow input rate is 0.5 uL/min and the PBS buffer flow input rate is 5 uL/min.

The two left, two middle and two right panels of FIG. 6 show the effect of separating blood cells by UHF bulk acoustic wave of power of 1660 mW, 417 mW and 208 mW, respectively. The boundary of the triangular bulk acoustic wave generation region (i.e., the direction of the vortex channel, which is the side of the triangle which is closer with the inlet) in the left panel of each two panels forms a larger angle with the flow direction of the liquid (i.e., laminar flow) in the microfluidic channel than that in the right panel.

The results are as shown in FIG. 6: the smaller the angle formed by the boundary line of the bulk acoustic wave generation region of said UHF resonator and the solution flow, the less the number of cells leaving the vortex channel, i.e., the more cells reach the downstream corner of the triangular vortex channel (i.e., the target cell release point) and leave the channel from there. It can be seen that the smaller the angle formed between the vortex channel and the flow direction of the laminar flow, the easier it is to keep the cells moving in the vortex channel, i.e., fewer cells are detached from the vortex channel, and the efficiency of separation is improved.

Thus, in one aspect of the present invention, the boundary line of the bulk acoustic wave generation region of said UHF resonator in the microfluidic system (i.e., the shape of the corresponding vortex channel) is set to be suitable for cells or vesicles to move down the vortex channel to the release point in the vortex channel. This prevents the cell or vesicle from leaving the vortex channel before arriving the release point.

In yet another aspect of the present invention, the cells or vesicles are kept in the vortex channel by adjusting the angle of the boundary line of the bulk acoustic wave generation region of said UHF resonator to the fluid channel and move to the release point. The inventors unexpectedly found that the smaller the angle formed between the boundary line of the bulk acoustic wave generating region and the fluid channel, the easier it is to keep the cells or vesicles moving in the vortex channel, i.e., fewer cells or vesicles leaving the vortex channel before arriving the release point and the efficiency of separation is improved.

In addition, as shown in FIG. 6, under the same conditions of other system parameters, the higher the power, the more cells reach the downstream angle of the triangular vortex channel (i.e., the cell release point) and leave from there, thus the higher the separation efficiency is achieved.

Figure 7:
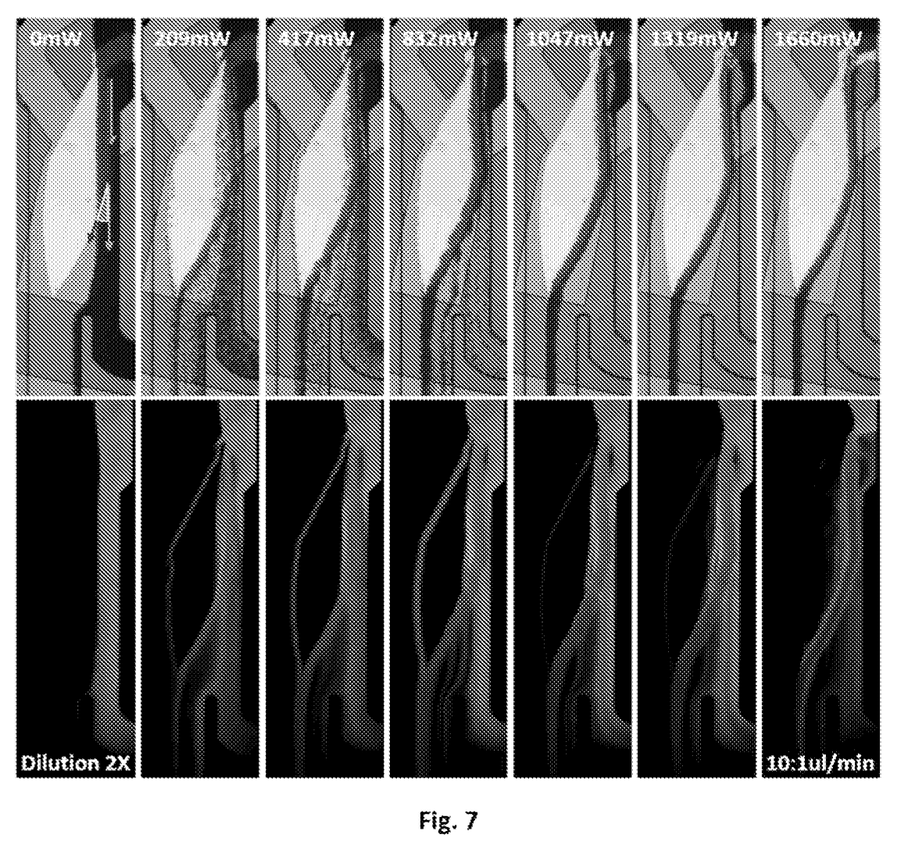
FIG. 7 shows the effect of different UHF bulk acoustic wave resonator settings on the separation of blood cells in whole blood.

Example 6 Effect of Different UHF Bulk Acoustic Wave Resonator Settings on the Separation of Blood Cells from Whole Blood A microfluidic channel was constructed as shown in FIG. 7. The surface of the UHF resonator (i.e., the bulk acoustic wave generation region, shown as a spindle-shaped device in the Figure) is located on one side of the microfluidic channel (right side of the Figure) and tilted to the left. The microfluidic channel is set up with two solution inlets. Whole blood sample is input through the right side inlet. PBS solution is input through the left side inlet. The blood sample flow is fully passed through the bulk acoustic wave generation region by adjusting the flow of PBS solution and the focusing effect of sheath flow. The downstream corner of the boundary of the spindle-shaped acoustic wave generation region (i.e., the location of the vortex channel) is the target cell release point, and the released cells leave from the downstream corner position and enter the cell outflow channel in the direction of the microfluidic channel.

The height of the said microfluidic channel is 50 um. The UHF bulk acoustic wave resonator frequency is 1.83 GHz, and the three output powers are shown in FIG. 7. The sample flow input rate is 1 uL/min and the PBS buffer flow input rate is 10 uL/min.

The spindle-shaped bulk acoustic wave generation region as shown in the Figure is divided into two regions, the focusing region (the upper half of the spindle-shaped device, whose right side boundary has the same direction as the laminar flow) and the sieving region (the lower half of the spindle-shaped device, whose right side boundary forms a large angle with the laminar flow direction). As shown in the Figure, in the upstream part of the device, the vortex tunneling direction is the same as the laminar flow direction, and the vortex drag force does not change the motion of the cells along the laminar flow direction, but only allows the cells to migrate laterally to the center of the vortex, i.e. focus the cells to the center of the tunnel. And in the sieving zone part, the cells focused to the vortex center can move more stably compared to the unfocused cells. Fluorescence was added to the blood to show the movement: 2 L of Calcein-AM was added to 1 mL of blood. As shown in the Figure, blood cells in the plasma were efficiently moved along the right border of the spindle device to the cell release point located on the left side of the flow channel, and left the spindle device at the cell release point and entered the PBS buffer.

It can be seen that, except for a small portion of plasma that move with the blood cells to the cell outflow channel due to adhesion to the cells, most of the plasma is recovered by entering the plasma recovery channel in the direction of the original liquid flow.

Thus, in one aspect of the present invention, the boundary line of the bulk acoustic wave generation region of said UHF resonator in the microfluidic system (i.e., the shape of the corresponding vortex channel) is set to be suitable for cells or vesicles to move down the vortex channel to the release point in the vortex channel. This prevents the cell or vesicle from leaving the vortex channel before arriving the release point.

In yet another aspect of the present invention, the cells or vesicles are kept in the vortex channel by adjusting the angle of the boundary line of the bulk acoustic wave generation region of said UHF resonator to the fluid channel and move to the release point. The inventors unexpectedly found that the smaller the angle formed between the boundary line of the bulk acoustic wave generating region and the fluid channel, the easier it is to keep the cells or vesicles moving in the vortex channel, i.e., fewer cells or vesicles leaving the vortex channel before arriving the release point and the efficiency of separation is improved. In the present invention, a preferred shape of the bulk acoustic wave generation region of the UHF resonator is spindle-shaped.

yet another aspect of the present invention, the bulk acoustic wave effecting region of the UHF bulk acoustic wave resonator in the microfluidic system has a focusing zone and a sieving zone. The focusing zone is located upstream of the bulk acoustic wave effecting region (i.e., near the direction of sample inflow and away from the release point), and the sieving zone is located downstream of the bulk acoustic wave action region (i.e., near the direction of sample outflow; nearer to or including the release point). The setup of the bulk acoustic wave effecting region in the focusing zone is more suitable to keep the flexible particles moving in the vortex channel compared to that of the sieving zone: cells or vesicles in the vortex channel in the focusing zone move along the same or similar direction as the flow direction and are subject to relatively less vortex dragging force, making it easier for the cells or vesicles to enter and remain in the vortex channel; in the downstream sieving zone, cells focused to the vortex center can move more stably along the vortex channel than unfocused cells. In yet another aspect of the present invention, the angle formed between the boundary line of the bulk acoustic wave effecting region and the fluid channel in the focusing zone is smaller than that in the sieving zone. For example, in the focus zone, the boundary of the bulk acoustic wave effecting region and the fluid channel direction is the same or basically the same (for example, the angle is less than 10°); the cells in this region of the vortex channel being effected by the vortex drag force which basically does not change the cell movement direction (i.e., the direction of the flow) but only let the cell move to the center of the vortex, thus achieve the focus of the cell; in sieve zone, angle between the boundary of the bulk acoustic wave effecting region and the fluid channel is bigger, the cells focused to the vortex center moves more stably in the vortex channel than the unfocused cells.

In addition, as shown in FIG. 7, under the same conditions of other system parameters, the higher the power, the more cells reach the downstream angle of the triangular vortex channel (i.e., the cell release point) and leave from there, thus the higher the separation efficiency is achieved.

Figure 8:
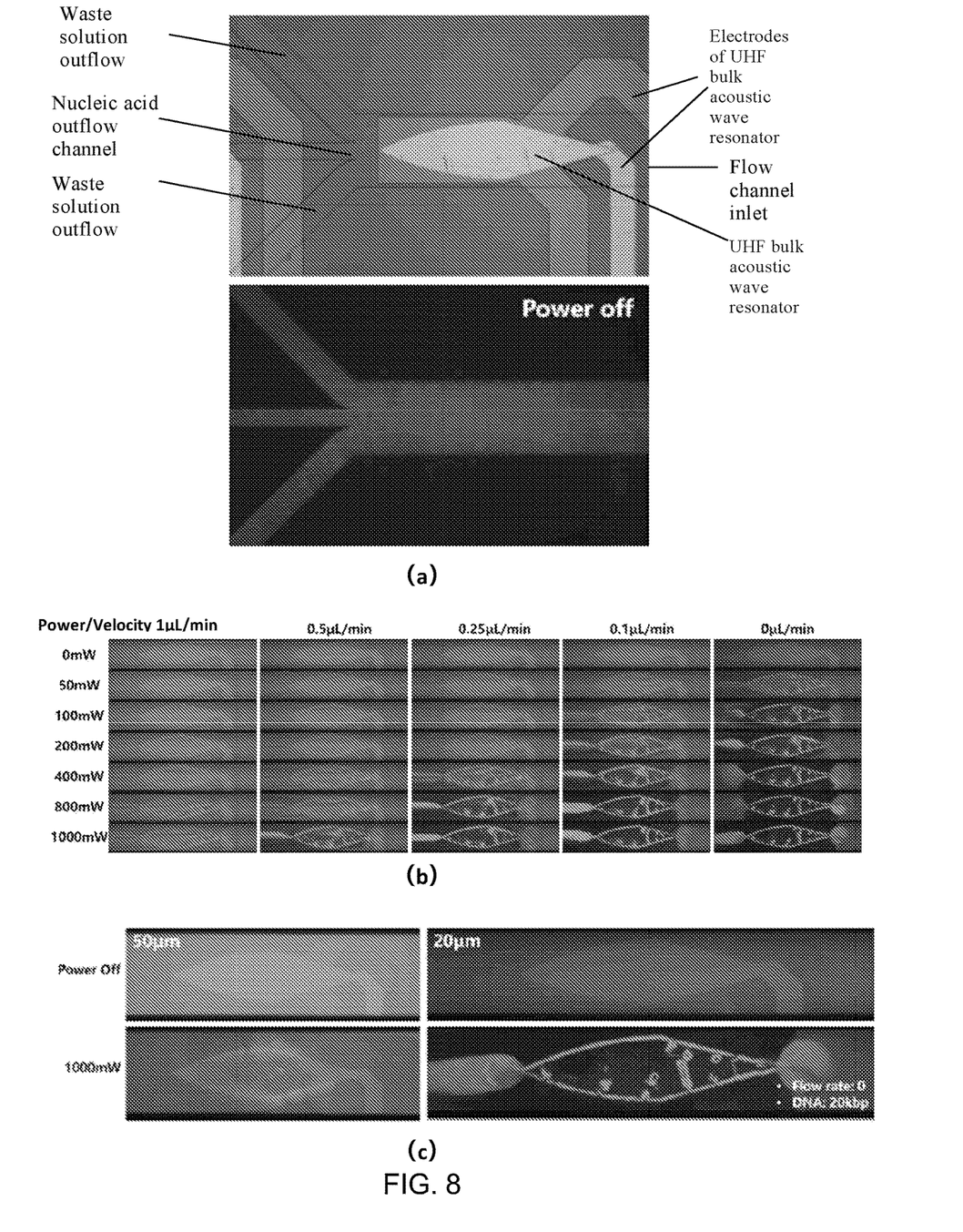
FIG. 8(a) shows the system setup and the observed phenomena after inputting the fluorescently stained nucleic acid solution.
FIG. 8(b) shows the movement of a double-stranded nucleic acid sample of size about 20 k in the device as shown in FIG. 8(a) at different flow rates and different bulk acoustic wave operating powers.
FIG. 8(c) shows the movement of a double-stranded nucleic acid sample of size about 20 k in the device as shown in FIG. 8(a) with different flow channel heights.
FIG. 8(d) shows the movement of a double-stranded nucleic acid sample of size about 5 k in the device as shown in FIG. 8(a) at different flow rates and different bulk acoustic wave operating powers.
FIG. 8(e) shows the movement of circular nucleic acid or a linear nucleic acid of about 5 k in size in the device as shown in FIG. 8(a).

Example 8 Control of Nucleic Acid Movement and Separation/Purification of Nucleic Acids A microfluidic channel and UHF resonator system as shown in FIG. 8(*a*) was prepared and set up according to the method described in Examples 1 and 2. FIG. 8(a) shows a top view of the device. The flow channel inlet is on the right side of the Figure for the input of PBS solution containing nucleic acid fragments of different sizes. The surface of the UHF resonator, i.e., the bulk acoustic wave generation region, is spindle-shaped as shown in the Figure, and its left tip is the nucleic acid release point. The left side of the microfluidic channel includes three outflow channels, the middle of which is the nucleic acid outflow channel, and the nucleic acid released from the nucleic acid release point at the left tip of the spindle shape enters the nucleic acid outflow channel. The upper and lower channels of the nucleic acid outflow channel are for solution outflow after removal of the target nucleic acid.

Nucleic acids are stained and quantified by the Qubit sDNA HS kit, which is dissolved with PBS solution. FIG. 8(a) shows the system setup and the observed phenomena after inputting the fluorescently stained nucleic acid solution: the upper panel shows the bright field and the lower panel shows the observed fluorescence signal, showing the uniform distribution of the fluorescently stained nucleic acid solution in the microfluidic channel when the UHF resonator is not operating.

FIG. 8(b) shows the movement of a double-stranded nucleic acid sample of size ~20 k in the device as shown in FIG. 8(a) at different flow rates (0, 0.1, 0.25, 0.5, 1 L/min) and different bulk acoustic wave operating powers (50-1000 mW). The fluid channel height was about 20 μm.

The nucleic acid was extracted sheep whole blood genomic DNA with a size of about 20 kbp.

As shown in FIG. 8(b), with a constant input of nucleic acid solution from the inlet of the flow channel and a continuous operation of the UHF resonator, the nucleic acid moves along the edge of the spindle-shaped UHF resonator device to the release point under suitable flow rate and bulk acoustic wave power conditions. The results demonstrate that the device and method of the present invention have good ability to control the movement of 20 kbp double-stranded DNA, and the control ability is positively correlated with the applied power and negatively correlated with the lateral fluid velocity in the flow channel. The present experiments are the results of continuous-operation-mode experiments, and it can be seen that no adhesion of nucleic acids in the UHF resonator device and flow channel and no agglomeration in the vortex occur in the continuous-operation-mode.

Based on the fluorescence signal, it can be seen that at a flow rate of 0.1 μL/min and a power of 1000 mW, continuous enrichment of all nucleic acids in the bulk acoustic wave device can be achieved, and the enrichment efficiency (i.e., the amount of nucleic acids entering the nucleic acid outflow channel over total input) exceeds 90%. In the vortex channel at the edge of the bulk acoustic wave region, 20 kbp DNA is enriched in approximately 35 μm diameter vortex tunnels. At the release site, the nucleic acid is released from the vortex and then diffuses into a strip of nucleic acid flowing downstream with a width of about 125 μm under the combined action of secondary vortex and lateral fluid.

FIG. 8(c) shows the movement of a double-stranded nucleic acid sample of size about 20 k in the device as shown in FIG. 8(a) with different flow channel heights (50 μm and 20 μm).

The results show that the system with a 20 μm height flow channel acts significantly more efficiently than the system with a 50 μm height flow channel under the same flow rate and power of the bulk acoustic wave action. This demonstrates that the reduced height of the microfluidic channel can improve the effectiveness of the acoustic resonator device in capturing small-sized particles. The reduced channel height increases the velocity gradient of the acoustic fluid vortex, and the aggregation of target particles at the center of the vortex is positively correlated with the gradient force of the vortex, thus improving the capture efficiency of the acoustic fluid. It can be seen from the above Figure that the range of vortices formed at the edge of the bulk acoustic wave in the flow channel at 50 m height is significantly larger than that in the 20 μm flow channel.

FIG. 8(d) shows the movement of a double-stranded nucleic acid sample of size about 5 k in the device as shown in FIG. 8(a) at different flow rates (0.1, 0.25, 0.5 L/min) and different bulk acoustic wave operating powers (50-1000 mW). The fluid channel height is ~20 μm.

The 5 k double-stranded nucleic acid samples were DNA plasmids, which were double-stranded circular DNA.

The results demonstrate that the apparatus and method of the present invention has good ability to control the movement of plasmid DNA of 5 kbp and the control ability is positively correlated with the applied power and negatively correlated with the lateral fluid velocity in the flow channel.

FIG. 8(e) shows the movement of circular nucleic acid or a linear nucleic acid of about 5 k in size in a device as shown in FIG. 8(a). The fluid channel height is about 20 μm.

The 5 k linear nucleic acid is a 5 k double-stranded nucleic acid sample which is a product of the DNA plasmid used in FIG. 8(d) being enzymatically cleaved and forming a double-stranded linear DNA.

The results show that the system has significantly better control on the 5 k circular nucleic acid than the linear nucleic acid of the same size at the same flow rate and bulk acoustic action power.

The above description is only an embodiment of the present invention and is not intended to limit the present invention. Any modification, equivalent replacement, improvement, etc. made within the spirit and principles of the present invention shall be included in the scope of protection of the present invention.

The invention claimed is:

1. A method for controlling the movement of target flexible particles in a solution, comprising:
   (1) allowing a solution containing flexible particles to flow through a microfluidic device, said flexible particles being nano- or micron-sized particles with deformation properties, said device comprising:
   a fluid channel having an inlet and an outlet;
   one or more ultra-high frequency (UHF) bulky acoustic wave resonators provided on a wall of said fluid channel, said ultra-high frequency bulky acoustic wave resonators being capable of generating bulk acoustic waves in said fluid channel with a frequency of about 0.5-50 GHz and transmitted to the opposite side of said fluid channel;
   (2) said UHF bulky acoustic wave resonator emitting a bulky acoustic wave transmitted to said wall on the opposite side of said fluid channel, producing a vortex channel in the solution defined by the boundary of the bulky acoustic wave generating region of the UHF resonator;
   (3) by the setting of the shape or position of the bulky acoustic wave action region of the UHF bulky acoustic wave resonator, allowing the flexible particles in the solution enter and move along the vortex channel and leave the vortex channel at a set position, which is called the release point, wherein a boundary line of the bulky acoustic wave generation region of said UHF resonator are set to be suitable for keeping the target flexible particles in the vortex channel while moving down along the vortex channel to the release point, by reducing the presence of a turn or curvature change in the boundary line of the bulky acoustic wave generation region.

2. The method of claim 1, wherein further comprising selecting the flexible particles entering the vortex channel by adjusting the power of the bulky acoustic wave and/or by adjusting the velocity of said solution flowing through the bulky acoustic wave region.

3. The method of claim 1, wherein there is a turn or curvature change in the boundary of the bulky acoustic wave generation region corresponding to said release point.

4. The method of claim 1, wherein keep the flexible particles in the vortex channel while moving to the release point by adjusting the angle formed by the boundary line of the bulky acoustic wave generation region of said UHF resonator and the fluid channel.

5. The method of claim 1, wherein the bulky acoustic wave action region of the ultra-high frequency bulky acoustic wave resonator comprises a focusing zone and a sieving zone, said focusing zone being located upstream of the bulky acoustic wave action region and said sieving zone being located downstream of the bulky acoustic wave action region, wherein the setting of the bulky acoustic wave action region of the focusing zone is more suitable for keeping the flexible particles moving in the vortex channel than that of the sieving zone.

6. The method of claim 1, wherein the power of the bulk acoustic wave generated by said UHF resonator is adjusted to be about 20-5000 mW.

7. The method of claim 1, wherein the velocity of flow of said solution through the bulk acoustic region is regulated to be about 0.01-10 mm/s.

8. The method of claim 1, wherein said flexible particles are cells or cell vesicles.

9. The method of claim 8, wherein the cells or cell vesicles have a diameter of about 0.01-30 μm.

10. The method of claim 1, wherein said flexible particles are nucleic acid molecules.

11. The method of claim 10, wherein the nucleic acid molecules are ≥300 bp in length.

12. The method of claim 1, wherein said fluid channel of said microfluidic device has a height of about 20-200 um.

13. The method of claim 1, which is used to separate different flexible particles in a solution.

14. The method of claim 1, wherein said fluid channel is divided into different regions wherein UHF resonators for separating different flexible particles are provided, said UHF resonators for separating different flexible particles may have differently shaped acoustic wave generation regions, or said UHF resonators may generate bulky acoustic waves of different power, or said different regions have different flow rates, or combinations thereof.

15. The method of claim 1, wherein said fluidic channel of said microfluidic device has an outflow channel for said target flexible particles being controlled to move, i.e. a particle outflow channel; and an outflow channel for a solution lack of or containing less of target cells or vesicles being controlled to move, i.e. a solution outflow channel.

* * * * *